United States Patent
Migliaccio et al.

(10) Patent No.: US 7,465,050 B2
(45) Date of Patent: Dec. 16, 2008

(54) METHOD AND APPARATUS FOR THREE-DIMENSIONAL VIDEO-OCULOGRAPHY

(75) Inventors: Americo A. Migliaccio, Owens Mills, MD (US); Charles C. Della Santina, Towson, MD (US); Hamish G. MacDougall, Woolloomooloo (AU)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/588,738

(22) PCT Filed: Feb. 4, 2005

(86) PCT No.: PCT/US2005/003780

§ 371 (c)(1),
(2), (4) Date: Aug. 4, 2006

(87) PCT Pub. No.: WO2005/077259

PCT Pub. Date: Aug. 25, 2005

(65) Prior Publication Data

US 2007/0177103 A1     Aug. 2, 2007

Related U.S. Application Data

(60) Provisional application No. 60/541,590, filed on Feb. 4, 2004.

(51) Int. Cl.
*A61B 3/14* (2006.01)
*A61B 3/10* (2006.01)

(52) U.S. Cl. .......................... 351/209; 351/213; 351/221

(58) Field of Classification Search ................. 351/205, 351/209, 213, 216, 221, 222, 233, 236, 245
See application file for complete search history.

(56) References Cited

U.S. PATENT DOCUMENTS 4,180,323 A * 12/1979 Persson et al. ................. 356/3
4,529,280 A *  7/1985 Nohda ......................... 351/211
7,234,815 B2 * 6/2007 Bees ........................... 351/213

* cited by examiner

Primary Examiner—Mohammed Hasan
(74) Attorney, Agent, or Firm—Larry J. Guffey

(57) ABSTRACT

A device for measuring the three-dimensional movements of an eye includes: (a) a mark array that identifies prescribed positions on the eye whose movements are to be measured, (b) a digital camera for capturing the two-dimensional images of this marker array as the eye is moved, (c) a light source that illuminates the marker array with an output that is outside the spectral range of the camera, (d) light source that are used to align the camera's optical axis with the center of the eye, (e) an algorithm for computing the three-dimensional positions of the marker array from the information contained in the captured digital images, and (f) a base for fixing the position of the camera relative to the position of the eye, wherein the materials of the marker array are chosen so that the array has the ability to, when illuminated as described above, give off energy that is in the spectral range of the device's camera.

20 Claims, 6 Drawing Sheets

FIG. 6b $$i = \sqrt{(eye\_radius\_in\_pixels)^2 - (j^2 + k^2)}$$

STEP 7

ONE IMAGE IS DEFINED AS THE REFERENCE IMAGE. FOR EXAMPLE "IMAGE 1" ABOVE. THE THREE-DIMENSIONAL COORDINATES OF EACH MARKER IN THIS IMAGE DEFINE THE REFERENCE OR ZERO POSITION OF THE MARKER ARRAY (AND EYE) AND ARE USED TO CONSTRUCT THE REFERENCE POSITION ROTATION MATRIX BELOW.

STEP 8

$$R = \begin{bmatrix} i_0 & i_1 & i_2 \\ j_0 & j_1 & j_2 \\ k_0 & k_1 & k_2 \end{bmatrix}_{REFERENCE}$$

THE THREE MARKERS IN EACH IMAGE ARE IDENTIFIED AS MARKER 0, MARKER 1 OR MARKER 2. A LEAST SQUARES ALGORITHM IS USED TO ENSURE THAT EACH MARKER IS CORRECTLY IDENTIFIED AFTER TRANSIENT LOSS OF MARKER TRACKING.

IMAGE n

STEP 9

FOR EACH IMAGE THE THREE-DIMENSIONAL POSITION OF EACH MARKER IS CALCULATED AND USED TO CONSTRUCT A CURRENT POSITION ROTATION MATRIX.

STEP 10

$$R = \begin{bmatrix} i_0 & i_1 & i_2 \\ j_0 & j_1 & j_2 \\ k_0 & k_1 & k_2 \end{bmatrix}_{CURRENT}$$

EYE POSITION (ROTATION MATRIX) IS DEFINED AS THE THREE-DIMENSIONAL ROTATION REQUIRED TO MOVE THE MARKER ARRAY (THREE MARKERS) FROM THE REFERENCE POSITION TO THE CURRENT POSITION.

STEP 11

$$\mathcal{R} = \begin{bmatrix} i_0 & i_1 & i_2 \\ j_0 & j_1 & j_2 \\ k_0 & k_1 & k_2 \end{bmatrix}_{CURRENT} * \begin{bmatrix} i_0 & i_1 & i_2 \\ j_0 & j_1 & j_2 \\ k_0 & k_1 & k_2 \end{bmatrix}_{REFERENCE}^{-1}$$

EULER ANGLES, FICK ANGLES, HELIOHOLTZ ANGLES, ROTATION VECTORS OR QUATERNIONS CAN BE CALCULATED FROM THE EYE ROTATIONMATRIX TO DESCRIBE EYE POSITION.

METHOD AND APPARATUS FOR THREE-DIMENSIONAL VIDEO-OCULOGRAPHY

CROSS-REFERENCE TO RELATED APPLICATION

This application claims the benefit of U.S. Provisional Patent Application No. 60/541,590, filed Feb. 4, 2004, by the present inventors and assigned to The Johns Hopkins University.

STATEMENT AS TO FEDERALLY SPONSORED RESEARCH

This invention was made with Government support under Grant No. K08-DC006216 to Dr. Della Santina, which was awarded by the National Institute On Deafness And Other Communication Disorders. The Government may have certain rights in this invention.

BACKGROUND OF THE INVENTION

1. Field of the Invention

This invention relates to oculography (i.e., eye movement recordings) and methods and devices for making non-contact measurements of the rotations of essentially spherical bodies. More particularly, the present invention relates to inexpensive, real-time, three-dimensional, video-oculography that utilizes a specialized marker array which is placed on the eye.

2. Description of Prior Art

Precise and accurate measurement of eye rotation is essential for the clinical evaluation and scientific study of vestibular (balance) and oculomotor (eye movement) disorders. Common types of such disorders often result in those afflicted reporting problems with dizziness.

The magnitude of such disorders can be noted by observing that over ninety million Americans suffer from dizziness; it is the ninth most common reason adults visit a primary care doctor. Thirty-four percent of Americans age 65-74 suffer from dizziness significant enough to limit their activities of daily life, making it the third most common medical complaint among this group; dizziness is the most common complaint in patients 75 years and older.

Eye rotation measurements are also important because they can be used in other applications, such as input to various computer systems for assorted purposes: data entry, command and control (e.g., navigation of computer-controlled equipment), communication, and the enhancement of virtual reality-based displays.

The "gold standard" method for measuring three-dimensional eye position is the scleral search coil technique. It involves search coils being either implanted on or affixed to the eye and their orientation identified by subjecting them to uniform, stable magnetic fields. However, even this method can suffer from a number of drawbacks that can affect measurement reliability (e.g., implantation of search coils can restrict or distort eye movements due to eye scarring and inflammation or coil lead tension, the imposed magnetic field can be distorted by metallic objects and by currents flowing in nearby equipment).

These drawbacks of the search coil technique have prompted efforts to develop video-oculographic (VOG) systems for the measurement of three-dimensional eye rotations. See FIG. 1 for a description of the coordinate system and the terminology used herein to describe rotational eye movements.

These systems typically make two-dimensional (horizontal and vertical) eye rotation determinations by tracking the pupil and/or a corneal reflection.

To determine eye rotations in a third dimension (torsional), most currently available VOG systems either track two or more landmarks on the eye or measure and track changes in iral contrast along a circular sampling path. In humans, pronounced iral striations make iral contrast tracking practical, whereas, in animals that do not have pronounced iral striations, it is more practical to track attached landmarks.

However, there are problems with these methodologies and the conventional VOG systems. For example, the quality of data using existing methods is often compromised due to misalignment of the camera with the eye. This misalignment can introduce errors >10%. Reflections of the light source on the eye and/or shading of the landmarks/pupil can produce either loss of the landmark or incorrect calculation of its centroid position. VOG techniques that track the pupil are inherently problematic because the contrast between the iris and pupil is not large. This non-exact demarcation zone makes it difficult to precisely define the pupil region and calculate the pupil centroid position.

Additionally, current three-degree eye measurement VOG systems that track landmarks on the eye employ complex and relatively inefficient algorithms. Most require considerable post-hoc processing of the data collected to enable computation of an eye's torsional movements. Meanwhile, those few systems that provide real-time measurements of eye torsional motions are prohibitively expensive for most clinical and diagnostic applications. Most of these commercial systems are for human applications only i.e. they track the pupil and iral signature. Given the same technological limitations pupil/iral tracking is significantly slower than landmark tracking.

Current methods and devices for measuring three-dimensional eye movements need to be improved by making them: (a) less expensive, (b) more portable so that such measurements can be made other than in only clinical laboratory settings, and (c) faster operating so to enable them to provide real-time measurements which can be more timely correlated for diagnostic purposes with the bodily motions which may be precipitating such eye movements.

The present inventors have been working in this technical field and towards the development of such improved methods and devices for some time. Much of their earlier research is applicable to the methodologies described herein and has been documented in the scientific literature. See for example: Migliaccio, MacDougall, Minor and Della Santina, "Inexpensive System for Real-Time 3-Dimensional Video-Oculography Using a Fluorescent Marker Array," submitted for publication to the Journal of Neuroscience Methods, Feb. 2004, and MacDougall, "The Human Eye-Movement Response To Maintained Surface Galvanic Vestibular Stimulation," Ph.D. dissertation, University of Sydney, May 2003.

3. Objects and Advantages

There has been summarized above, rather broadly, the background that is related to the present invention in order that the context of the present invention may be better understood and appreciated. In this regard, it is instructive to also consider the objects and advantages of the present invention.

It is an object of the present invention to provide improved, lower cost methods and devices for making eye rotation measurements.

It is another object of the present invention to provide improved, more portable methods and devices for making eye rotation measurements.

It is yet another object of the present invention to provide improved, faster operating methods and devices for making eye rotation measurements.

It is a further object of the present invention to provide improved diagnostic methods and devices for assessing vestibular and oculomotor disorders.

It is also an object of the present invention to provide improved methods and devices for providing eye rotation measurement input to various computer systems for a wide assortment of applications (e.g., data entry, command and control, communication, and the enhancement of virtual reality-based displays).

These and other objects and advantages of the present invention will become readily apparent as the invention is better understood by reference to the accompanying summary, drawings and the detailed description that follows.

SUMMARY OF THE INVENTION

Recognizing the needs for the development of improved methods and apparatuses for making eye rotation measurements, the present invention is generally directed to satisfying the needs set forth above and overcoming the disadvantages identified with prior art devices and methods.

In a first preferred embodiment, such a method for measuring the three-dimensional movements of an eye includes the steps of: (a) marking an array of positions on the eye whose movements are to be measured, (b) illuminating this marker array with a light source whose output is in a prescribed first spectral range, (c) capturing along a prescribed optical axis the two-dimensional, digital images of this array of eye-marked positions as the eye is moved, wherein these images are captured in a second spectral range that does or does not overlap with the illumination's prescribed first spectral range, (c) wherein this prescribed optical axis having been aligned with the center of the eye, and (d) computing the three-dimensional positions of the array of eye-marked positions from the information contained in the captured digital images.

In a still further preferred embodiment, the present invention takes the form of a device for measuring the three-dimensional movements of an eye. This devices includes: (a) a marker array that identifies prescribed positions on the eye whose movements are to be measured, (b) a digital video camera for capturing the two-dimensional, digital images of this marker array as the eye is moved, (c) a light source that illuminates the marker array with an output that is outside the spectral range of the camera, (d) light sources that are used to align the camera's optical axis with the center of the eye, (e) an algorithm for computing the three-dimensional positions of the marker array from the information contained in the captured digital images, and (f) a base for fixing the position of the camera relative to the position of the eye, wherein the materials of the marker array are chosen so that the array has the ability to, when illuminated as described above, give off energy that is in the spectral range of the device's camera.

Thus, there has been summarized above, rather broadly, the present invention in order that the detailed description that follows may be better understood and appreciated. There are, of course, additional features of the invention that will be described hereinafter and which will form the subject matter of any eventual claims to this invention.

BRIEF DESCRIPTION OF THE DRAWINGS

FIGS. 6a-6b illustrate the eye rotational position calculation aspects of the present invention.

DETAILED DESCRIPTION OF THE PREFERRED EMBODIMENT

Figure 1:
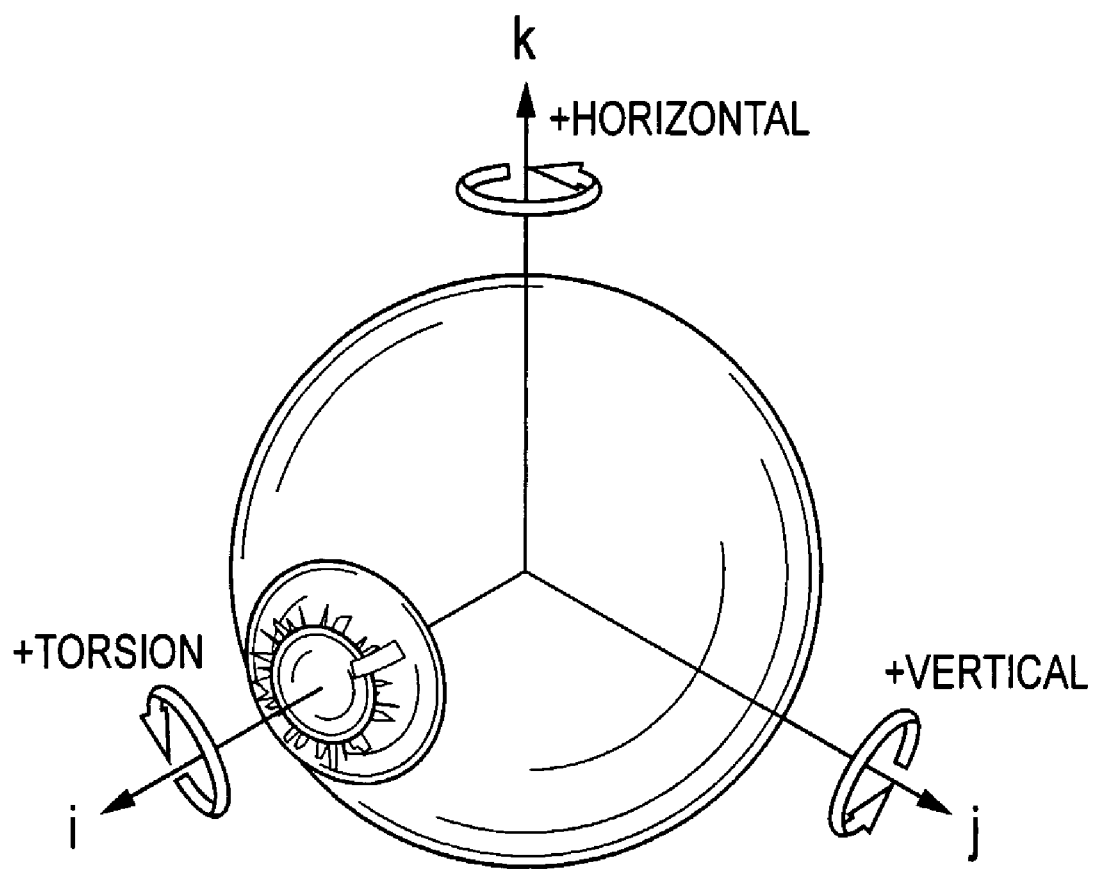
FIG. 1 displays the coordinate system and illustrates the terminology used herein to describe rotational eye movements.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention.

Described herein is an inexpensive technique and device 1 for the real-time measurement of three-dimensional eye position. In a preferred embodiment, it uses a digital video camera 2 with a modified lens 4 to track an array of three 1 mm×1 mm markers 6 on a piece of plastic film 8 that is affixed to the cornea or sclera of the eye. Depending on the spectral sensitivity of the specific camera 2 used, an optical filter or filtering mirror 10 can be used to improve the contrast observed by the camera.

To increase contrast between the markers 6 and unwanted corneal reflections, the markers 6, in a first preferred embodiment, can be fabricated from materials that give them a fluorescent property. The markers are illuminated with an ultraviolet light source 12 whose output is outside the camera's range of spectral sensitivity.

The experimental arrangement and alignment of the camera with respect to the eye whose motions are to be measured is critical to achieving accurate measurements.

In a preferred embodiment of the present invention that is suitable for use in animal experiments, this desired alignment is achieved by using a suitable head mounting apparatus 14. Connected to this apparatus 14 is a base 16 which provides the means on which to mount the camera so that it is pointing through the center of the eye.

Figure 2A:
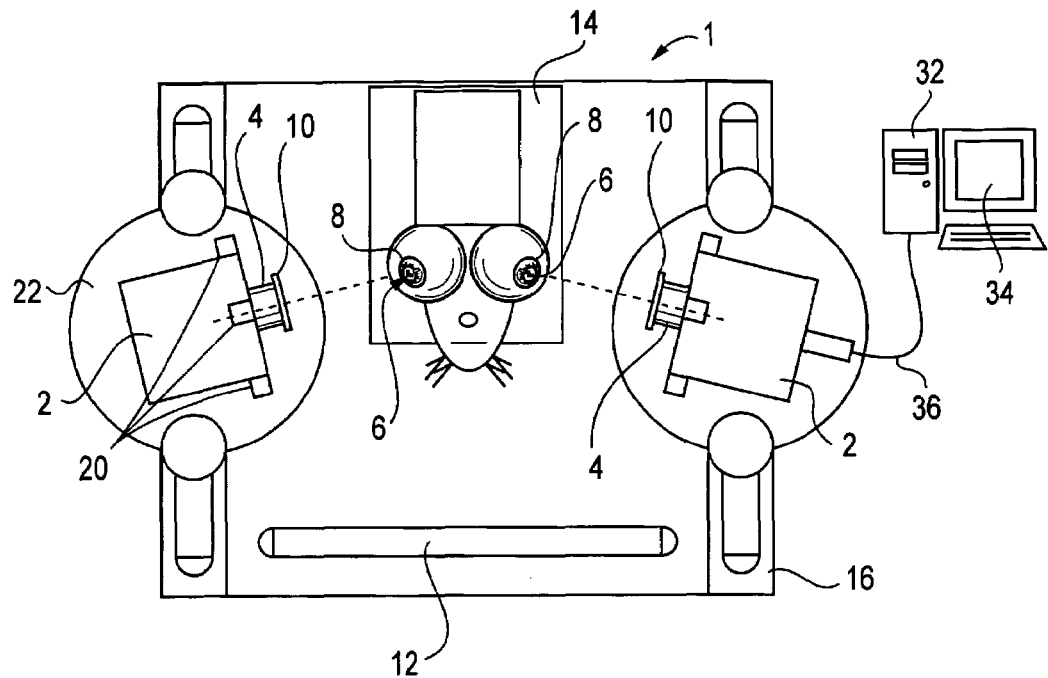
FIGS. 2a and 2b are schematic top and front views of an experimental set-up of a preferred embodiment of the present invention that has been configured to allow for the eye rotation measurements of a laboratory animal.
Figure 2B:
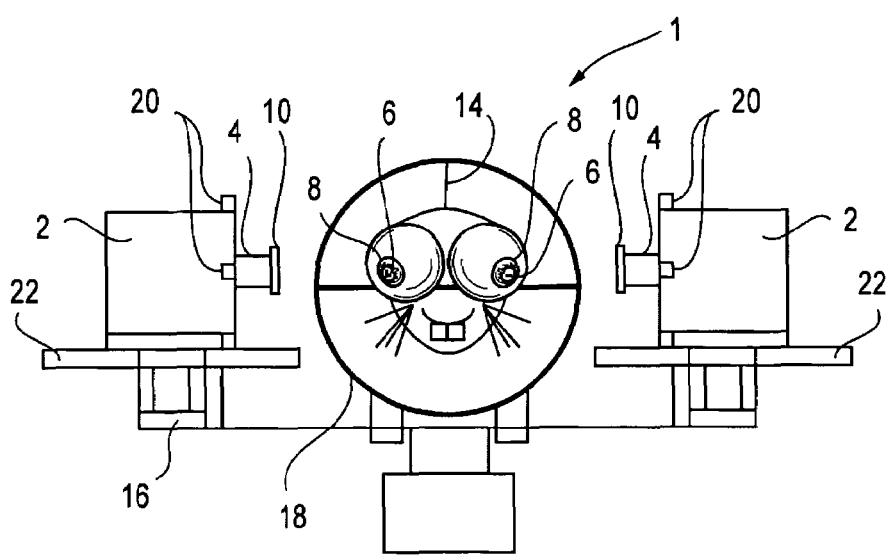

See FIGS. 2a and 2b for schematics of the experimental set-up of the present invention when the head mounting apparatus and base are configured to accommodate a laboratory animal whose eye rotations are to be measured in response to various applied stimuli. In this situation a gimbal device 18 is used to hold the animal.

In this experimental setup, care must be taken to minimize possible translational and angular alignment errors between the camera 2 and the targeted eye. Translational misalignment occurs when the camera 2 is not pointing through the center of the eye. To achieve the necessary translational alignment, four alignment light sources 20 (e.g., 3 mm diameter white LEDs, NSPW300BS, Nichia Tokushima, Japan) are positioned around the camera 2 in the form of a right-angle cross, with the light sources 20 facing the eye and equidistant from the center of the lens. It should be noted that these alignment light sources could also be placed at differing prescribed distances from the optical axis and they could still be used to assist in providing translational alignment, but with a slightly more complex alignment procedure. Also, it is not absolutely necessary to use four light sources, as two symmetrically placed light sources or a single light source, with its image centered on the camera lens by using a partial mirror, could also be used.

Translational alignment can be, achieved by noting that when the camera's optical axis is perfectly orthogonal to a targeted spherical, symmetric, convex reflective surfaces (such as an eye), the four LED reflections seen in the video image are centered on and equidistant from the center pixel of the image. If the camera 2 is tilted with respect to the imaged surface, the LED reflections are no longer equidistant from each other, and the center of the cross they define is no longer aligned with the center pixel of the image. The mounting of the camera to the base is such as to provide the necessary flexibility in its orientation so as to ensure in a pre-test calibration that the reflections seen in the video image are centered on and equidistant from the center of the image. Alternatively, as in the animal experiments, the device holding the animal may provide the means for achieving this desired alignment.

Pure angular misalignment occurs when the camera 2 is pointing through the center of the eye, but the camera coordinate system is not rotationally aligned with the reference coordinate system. In the animal experiments conducted in support of this development effort, the reference coordinate system aligns with the animal's head (specifically, with the plane through the animal's horizontal semicircular canals, the midsagittal plane, and the coronal plane orthogonal to these), which in turn is aligned with the head mount apparatus 14. To ensure correct angular orientation of the cameras with respect to the base (and thus to the animal's head), each camera 2 is mounted on a rotating turret 22 that is adjustable in azimuth and elevation.

Each turret 22 maintains the torsional position of the camera 2 at zero degrees with respect to the head coordinate system. The azimuth and elevation of the camera 2 with respect to this system can be measured with a protractor to an accuracy of 0.25°. These angles are used to convert measured eye rotations into the head coordinate frame of reference.

It can be noted that such angular misalignment errors can be corrected by multiplying each rotation matrix representing instantaneous eye position by the matrix describing rotation from the incorrect frame of reference to the correct frame of reference.

Mixed angular plus translational misalignment occurs when the camera 2 is first brought into perfect alignment and then is rotated so that the camera's optic axis changes direction and no longer points through the center of rotation of the eye. The error due to this combined misalignment can be corrected post-hoc if the translational and angular deviation from the ideal camera position are known.

Figure 3A:
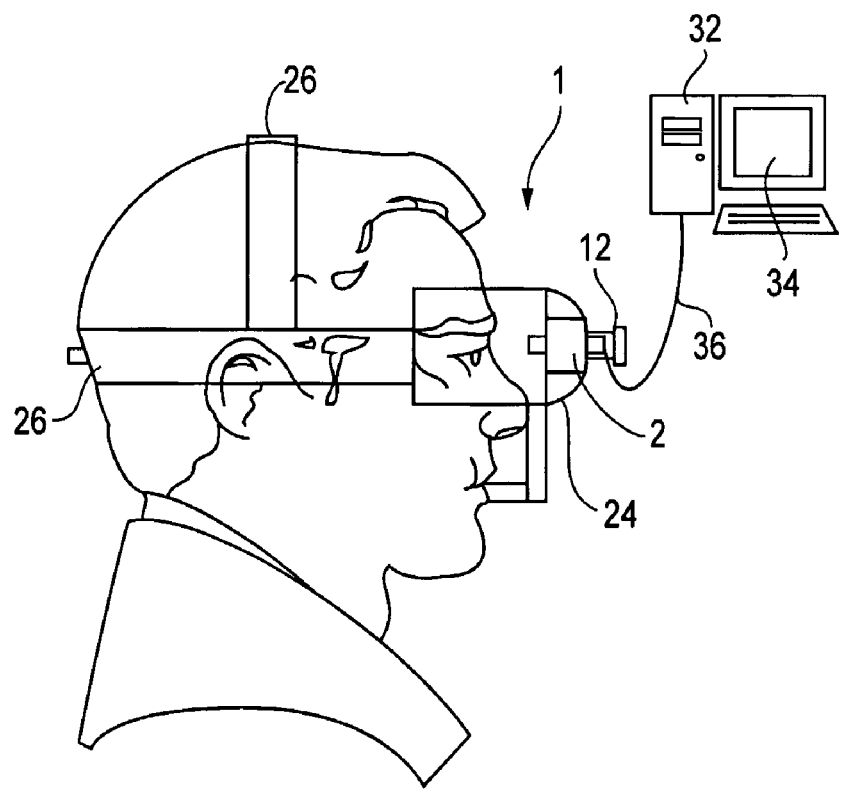
FIGS. 3a and 3b are schematic side and top views of an experimental set-up of the present invention that has been configured to allow for eye position measurements in humans.
Figure 3B:
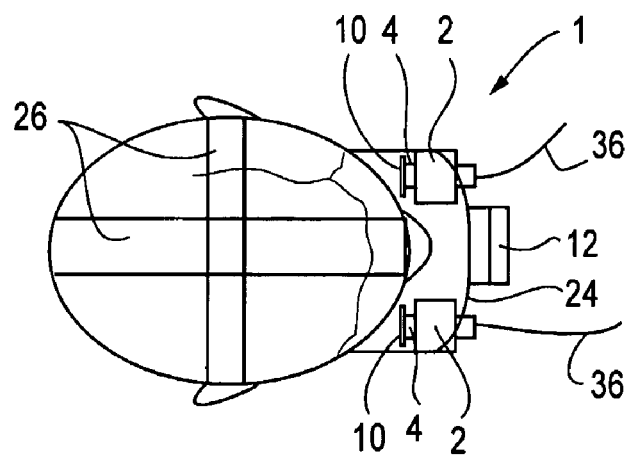

FIGS. 3a and 3b present schematic side and top views of an experimental set-up of the present invention that has been configured to allow for eye position measurements in humans. Again, the basic parts of the present invention are seen to be a digital video camera 2 with a modified lens 4 and optical filter 10 that are used to track an array of three 1 mm×1 mm markers 6 positioned on the cornea of the patient's eye and illuminated with a suitable light source 12.

In this embodiment, a suitable eye-mask type configuration 24, with its head mounting straps 26, is used to mount and orient the camera 2 and light source 12 in front of the eye whose motions are to be measured. Alignment lights 20 (e.g., LEDs which may be visible, infrared or ultraviolet light) are symmetrically positioned about the camera optical axis and are here shown to be mounted on the camera's housing, but may also be mounted in other positions sufficient to illuminate the eye (e.g., on an inner surface of the mask or external to the mask).

Figure 4:
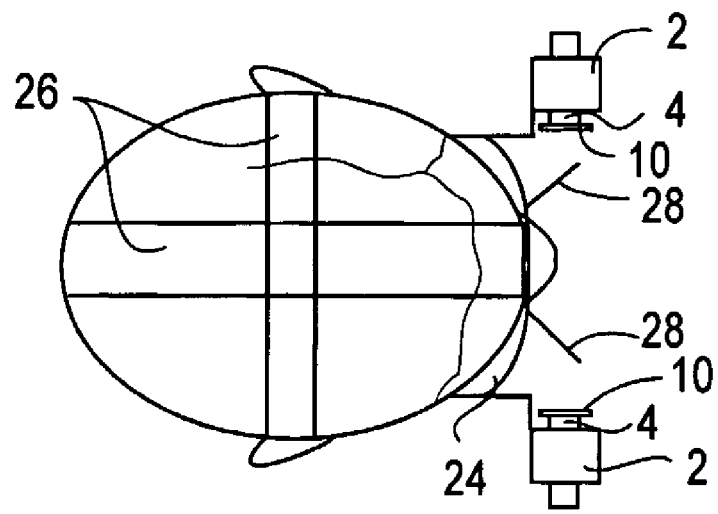
FIG. 4 is a schematic of another embodiment of the present invention that is suitable for measuring human eye movements in those instances in which it is desired to not obstruct the patient's view.

Shown in FIG. 4 is another embodiment suitable for measuring human eye movements in those instances in which it is desired to not obstruct the patient's view. In this embodiment, a mirror 28 which is partially transparent is mounted and aligned in front of the patient's eyes in such a manner that it allows the camera to be mounted to the side of the patient's eyes.

It should be recognized that there exist many alternative ways to mount a camera attached to a suitable head device or mask so that eye movements can be tracked and recorded. For example, a camera could be mounted down nearer a patient's cheeks so that the camera looks up into the eyes and doesn't obstruct one's straight ahead vision. All such camera orientations and consequent modifications of the mask or head device are considered to come within the realm of the current invention.

It can be noted that the development of a high frame rate version of the present invention has been facilitated by recent advances in complementary metal oxide semiconductor (CMOS) imaging technology, digital video cameras and computer interfaces.

CMOS imaging technology has, for many years, been considered to be inferior to charge-coupled devices (CCD). However, CMOS technology does have one major advantage over CCDs in that it can be manufactured using the same methods and equipment used for normal silicon chip production. For this reason CMOS technology is cheaper and evolves at a much faster rate than CCD sensors, which can only be made by a small number of large manufacturers. The quality of video images produced by CMOS sensors is now as good as, or in some cases better than, those from CCDs.

CMOS technology also allows for the integration of video processing on or near the sensor itself. This processing provides the opportunity to simplify the eye movement analysis task by shifting some of the processing burden on to the camera hardware and off the computer CPU. Tasks such as the automatic adjustment of brightness and contrast, the dynamic modification of look-up tables, conversion to bitmap, and variable region of interest can all be done in the camera.

Another important development in camera technology is the increasing use of digital imaging systems. Digital video cameras digitize on or close to CMOS or CCD and avoid the problems of noise and interference inherent to systems that pass analogue video signals down long leads. Digital video cameras are proving to be smaller, lighter and cheaper, and have lower power consumption than an equivalent combination of analogue camera and acquisition card for digital-to-analogue conversion.

Digital cameras can interface directly with a number of high-speed bus types, including Firewire (IEEE1394) and USB 2.0 that are standard, built-in features of recent PC and Macintosh computers. Because laptop computers also incorporate these high-speed bus technologies, eye movement recording systems can now become truly mobile.

A laptop, notebook or sub-notebook computer can analyze or store video data from a camera without any external source of power. This means that video eye movement analysis systems can now be used at a patient's bedside in the clinic or carried by a freely moving subject untethered to an experimental apparatus.

The biggest advantage of digital camera systems for eye movement analysis may be that they avoid the limits imposed by analogue video standards. It is possible to exceed the 25-30 Hz frame rates of domestic video equipment by: (a) de-interlacing frames into two fields, (b) using special double-speed cameras with more than one analogue video output, (c) using multiple digital to analogue converters, and (d) modifying camera electronics. These methods are complicated, processor intensive, and often very expensive because there is a small market for this esoteric equipment. Digital cameras can be programmed to transfer images of arbitrary size, adjustable pixel depth, variable region of interest, and have frame rates limited only by the bandwidth of their digital hardware. Since the Firewire bus permits a throughput of 400 Mbps and a UBS 2 a throughput of 480 Mbps, a high fame rate is possible, especially by transferring to the computer only the region of the image that is useful for eye movement analysis.

These advancements have been especially important in the development of portable eye movement measurement systems suitable for use with humans. This portability has been made possible by the development of the above described, new digital (IEEE 1394, "Firewire" or USB 2.0) camera technology. These cameras can be directly connected to signal and power via the Firewire port on laptop computers so as to yield a stand-alone, wireless and battery-powered eye movement analysis system that is capable of processing eye movements at 30 Hz online and in real time. The use of notebook computers and even the new sub-miniature notebook computers (e.g., Sony PictureBook which weights less than 1 kg) hold the promise of adding even more portability to such systems.

A camera 2 suitable for use in the system of the present invention was found to be an IEEE 1394 Firewire webcam (PYRO1394 WebCam, ADS Technologies, USA) retrofitted with ¼" format 16.0 mm focal length, f/2.0 C-mount board lens (BL160, Allthings Inc., Australia). This camera was used to acquire 640×480 pixel B&W (8-bit) images at 30 Hz.

For use with such a camera and a 16 mm lens 4, a 5 mm plastic spacer is placed between the lens housing and the printed circuit board of the webcam so as to allow the camera to be focused on a point 50 mm away.

National Instruments LabVIEW 7.0, NI-IMAQ Vision 7.0.1 and NI-IMAQ for IEEE 1394 Cameras 1.5 standard modules were used to control camera settings such as contrast and brightness and to correct for lens distortion and perspective.

Standard NI-IMAQ modules were used to change the image threshold so that only the markers 6 were visible on a black background and to determine the center of each marker using a center of mass algorithm.

Camera magnification is set so that the medial and lateral canthi are at the edges of the video image. Pixel size was calibrated using a known distance between markers 6 and verified by using a micrometer.

Appropriate light sources 12 for this system include a diffuse ultraviolet (UV-A) light source (360 nm peak, 9 Watt, FPX7BLB, Ushio Inc., Japan) or 80 nm UV-A light-emitting diodes (LEDs) (SSL-LX5093SUVC, Lumex Inc.).

Depending on the spectral sensitivity of the specific camera used, a UV cut filter 10 (SKYLIGHT 1B Hoya, Japan) or a yellow pass filter (K2 yellow filter Hoya, Japan) can be used to improve contrast. No filter was necessary when the webcams described above were used because their color CCD is already less sensitive to UV than most monochrome image sensors.

The maximum allowable exposure of UV-A (320-400 nm) that will not harm the eye (cornea and lens) for human use is 1 $J/cm^2$. The "black light" or UV-A lamp (sometimes called a "Wood's Lamp") that was used in this invention's development work is not considered hazardous because the UV-A radiance at the lamp surface is only about 3 $W/cm^2$. At 30 cm distance the UV-A radiance at the eye surface is about 50 $\mu W/cm^2$ and would require >five hours exposure to reach 1 $J/cm^2$. The UV LED light source generates about 3 mW, the beam angle was 30° so at 20 cm the UV-A radiance at the eye surface was about 33 $\mu W/cm^2$ and would require >eight hours to reach 1 $J/cm^2$.

A number of types of markers 6 are suitable for use with various preferred embodiments of the present invention. For example, one could use the previously described array of three 1 mm×1 mm markers 6 on a piece of plastic film 8 that is affixed to the cornea of the eye. Alternatively, one could, in certain circumstances, forego the use of an affixed marker array and instead tattoo or etch markers 6 onto the eye.

The markers 6 of the present invention are chosen so as to allow for the use of optical methods that increase marker signal-to-noise ratios above that of corneal reflections.

Figure 5:
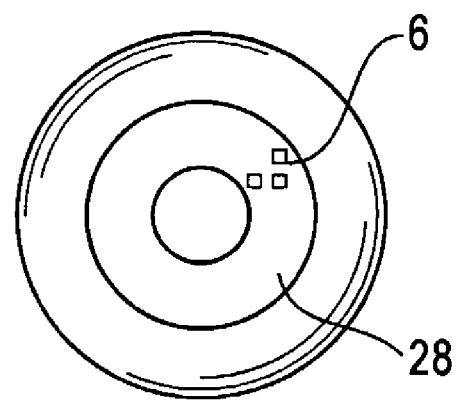
FIG. 5 illustrates a marker array of the present invention in which the array is place on an annular contact lens which is to be worn by the patient whose eye movements are to be measured.

One such technique involves using a fluorescent marker array illuminated by UV-A light source. This array can be fabricated using plastic film 8 laminated on paper saturated with fluorescent yellow ink. The film is opaque except for three transparent 1 mm×1 mm windows separated by 1 mm and arranged in a 45° right triangle [∴]. The distance between the windows of the plastic ink backing tape is fixed at 1 mm. For experiments requiring intact vision, the marker array is placed away from the pupil, or on an annular contact lens 30 and is illuminated with a UV-A light source. See FIG. 5.

Alternatively, a marker array using anti-Stokes (or 'up-converter') fluorescent pigments may be used with infrared illumination. In contrast to most fluorescent pigments, which can only emit wavelengths longer than those they absorb, anti-Stokes pigments emit visible light under infrared illumination (inorganic oxisulphide emits at 550 nm). As with the UV-fluorescent markers described above, the spectral shift between the infrared illumination source and the marker emissions still allows the use of optical filters to remove corneal reflection artifacts. This approach has the additional benefit that the marker array need not be positioned over the pupil for experiments that require absence of visual input, because the infrared light sources are not visible.

Another marker possibility, especially suited for use with humans, is the construction of a silicone scleral "contact lens" with fluorescent markers 6 embedded into such lens.

The data acquisition and analysis task of the present invention was accomplished with the use of the Pentium IV 2.4 GHz 1 GB RAM computer processor 32 of a desktop personal computer running Windows 2000. This hardware and the appropriate software allowed binocular, three-dimensional eye positions to be computed and displayed in real-time using an intuitive graphical user interface 34. The LabVIEW G programming language (National Instruments, Austin, Tex.) can be used to simplify the invention's software development.

The three-dimensional eye rotation necessary to move a marker array from a reference position to a final position is calculated in the present invention by using a mathematical method that is simpler and more efficient than others previously used.

Assuming the eye is a sphere that rotates about its center (or more precisely, that as the marker array moves with the eye, it travels along a spherical surface of radius approximately equal to that defined by the eye's globe-shaped outer surface), assuming the eye is centered on the camera's optical axis, and defining the center of the eye as the origin of a coordinate system (i, j, k), one can calculate the position in space of each marker. See FIG. 1.

The marker array can be positioned anywhere on the eye as long as it remains visible during eye rotations. The i, j and k axes measure translation of each marker in space, with j and k equaling the horizontal and vertical positions of each marker (measured in pixels) from the center of the video image, and i being the distance from the globe center to the marker along the optic axis of the camera. The i coordinate is calculated from j and k and the known radius of the eye as follows:

$$i = \sqrt{((eye\_radius\_in\_pixels)^2 - (j^2 + k^2))}$$

The rotation matrix $\mathcal{R}$ uniquely describing the eye rotation required to move the three markers from one position to another is:

$$\mathcal{R} = \begin{bmatrix} i_0 & i_1 & i_2 \\ j_0 & j_1 & j_2 \\ k_0 & k_1 & k_2 \end{bmatrix}_{current} * \begin{bmatrix} i_0 & i_1 & i_2 \\ j_0 & j_1 & j_2 \\ k_0 & k_1 & k_2 \end{bmatrix}_{ref}^{-1}$$

The subscript ref refers to the marker position before a rotation and defines the reference or zero rotational position of the eye. The subscript current refers to the marker positions in 3-D space after a rotation. Euler angles, rotation vectors and quaternions are calculated directly from the rotation matrix; see previously referenced Migliaccio and Todd, 1999.

Figure 6A:
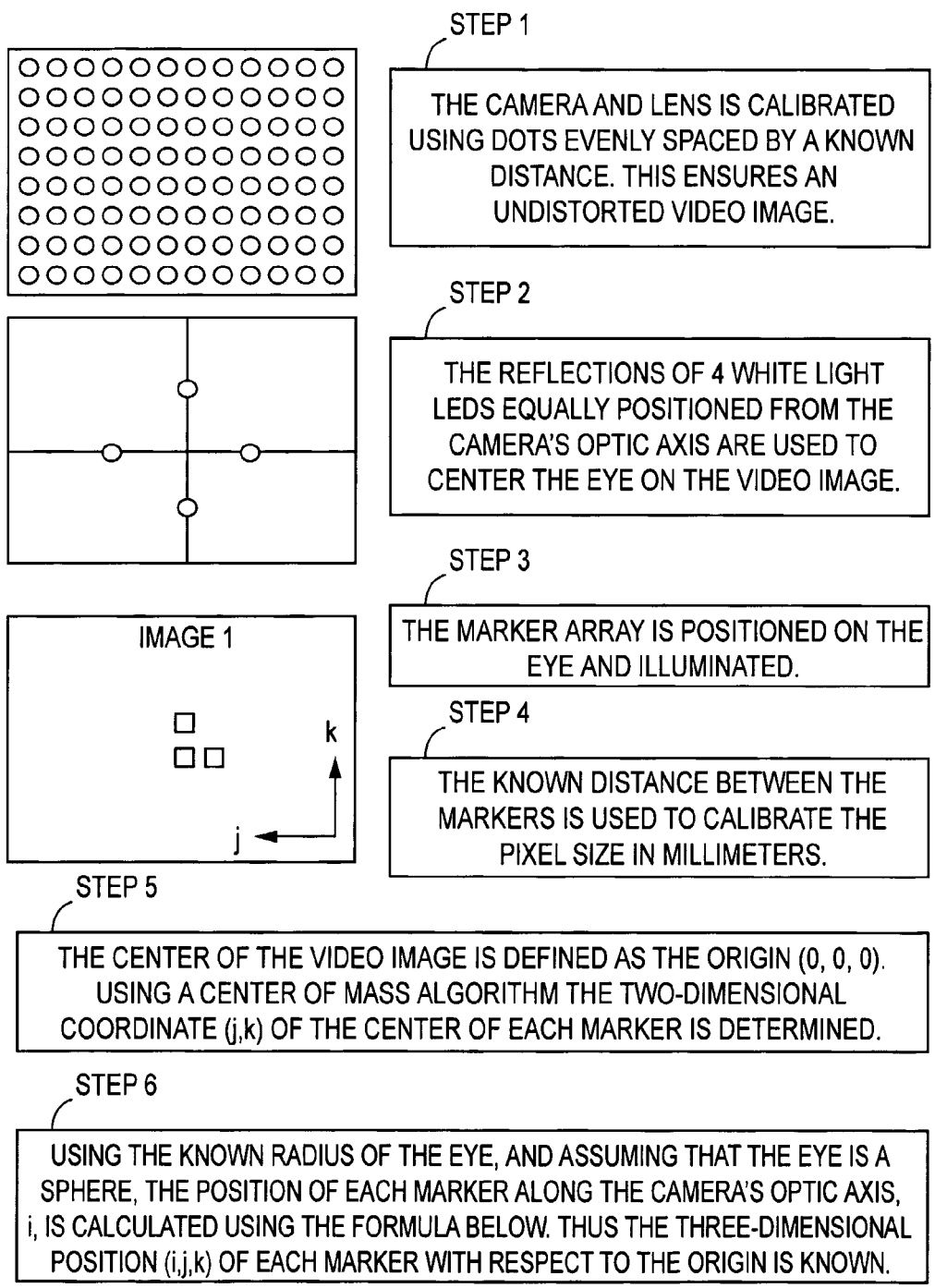

The steps in the above eye position calculation aspect of the present invention are further illustrated in FIGS. 6a-6b. The images shown in these figures were obtained from a digital camera as described herein and connected to a personal computer via a IEEE1394 Firewire bus 36.

Using 640×480 pixel cameras and magnification optimized so that the marker array range of motion filled the camera image frame, the absolute resolution of an experimental system that was assembled to demonstrate the feasibility of the present invention (assuming minimum detectable image shift of one pixel) was found to be <0.2°.

As previously mentioned, the accuracy of the above algorithm depends on alignment of the camera center with the center of the eye, which was ensured using the techniques described above. If unusual circumstances dictate that the camera cannot be precisely aligned with eye (e.g., in an experimental apparatus with limited space for camera placement), translational and angular misalignment can be corrected post hoc if the misalignment is known.

The correction must be in the following sequence. First, translational misalignment can be corrected by redefining the image center so that rather than using the default (center pixel of the camera image), the image pixel that aligns with the center of rotation of the eye is defined as the origin. Second, angular misalignment can be corrected by multiplying each eye rotation matrix by the inverse rotation matrix describing camera rotational position in the reference coordinate frame (whether head or superstructure/test-apparatus coordinates).

Tracking of one or more markers may be transiently lost during a blink, burst of saccades or extreme eye deviation that moves the markers behind the retracted eyelid or into a poorly illuminated region. Upon subsequent reacquisition of the marker image, potential uncertainty exists regarding which marker is which.

One approach to resolving this ambiguity would be to separately track each marker using different colors, shapes, sizes or relative positioning in the marker array. Alternatively, if the eye is assumed to stay within the ~45° oculomotor range, then only one of six possible permutations gives the correct pairing of all three markers from one image to the next, even if intervening images have been lost.

In experiments conducted to prove the feasibility of the present invention, the correct pairing was determined by calculating the summed square of marker travel distances for each permutation and accepting the permutation that resulted in the smallest value. The correct permutation was always selected, regardless of the cause or duration of transient marker image loss.

Because binocular video analysis is computationally intensive, the code written for the data analysis was optimized using NI-IEEE 1394 software interrupts, freeing the CPU for other processing until a new video image was acquired. Camera output was time-shifted to account for the delay between image acquisition at the image sensor and arrival of the new image in PC memory. This delay was found to be 33.2±0.1 ms by measuring the time delay between actual and VOG-derived motion of a digitally-controlled motor turning a simulated eye tracked by the VOG system continuously for five minutes.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention.

We claim:

1. A device for measuring the three-dimensional, rotational movements of an eye, said device comprising: a means for marking an array of positions on said eye whose rotational movements are to be measured, a means for capturing the two-dimensional, digital images of said array of eye-marked positions as said eye is moved, said image capturing means having an optical axis and a prescribed spectral range, a means for illuminating said marker array with a light source whose output is in a spectral range that is chosen from the group consisting of those that are either within or outside of said spectral range of said image capturing means, a means for aligning said optical axis of said image capturing means with the center of said eye, and a means for computing the three-dimensional rotational movements of said array of eye-marked positions from the information contained in said captured digital images.

2. The device as recited in claim 1, further comprising a means for fixing the position of said image capturing means relative to the position of said eye whose movements are to be measured.

3. The device as recited in claim 1, wherein said alignment means including an alignment light source.

4. The device as recited in claim 2, wherein said alignment means including an alignment light source.

5. The device as recited in claim 1, wherein said array marking means including a fluorescent pigment.

6. The device as recited in claim 5, wherein said array illuminating means including an ultra-violet light source.

7. The device as recited in claim 2, wherein said array marking means including a fluorescent pigment.

8. The device as recited in claim 7, wherein said array illuminating means including an ultra-violet light source.

9. The device as recited in claim 3, wherein said array marking means including a fluorescent pigment.

10. The device as recited in claim 9, wherein said array illuminating means including an ultra-violet light source.

11. The device as recited in claim 1, wherein said array marking means including an anti-Stokes fluorescent pigment.

12. The device as recited in claim 11, wherein said array illuminating means including an infrared light source.

13. The device as recited in claim 2, wherein said array marking means including an anti-Stokes fluorescent pigment.

14. The device as recited in claim 13, wherein said array illuminating means including an infrared light source.

15. The device as recited in claim 3, wherein said array marking means including an anti-Stokes fluorescent pigment.

16. The device as recited in claim 15, wherein said array illuminating means including an infrared light source.

17. The device as recited in claim 1, wherein said means of marking an array of positions on said eye whose movements are to be measured having three markers arranged in a 45 degree right triangle.

18. The device as recited in claim 17, wherein said means of computing the locations of said markers having an algorithm having a rotation matrix that describes the eye rotation required to move said markers from a first position to a second position.

19. The device as recited in claim 1, wherein said image capturing means having a digital camera, a computer processor and a high-speed interfacing device that connects said camera and said processor.

20. The device as recited in claim 19, wherein said processor being configured to fit within a computer chosen from the group herein described as a desktop, laptop, notebook or sub-miniature notebook.

\* \* \* \* \*